(12) United States Patent
Hong et al.

(10) Patent No.: US 10,196,437 B2
(45) Date of Patent: Feb. 5, 2019

(54) ANTIBODY BINDING SPECIFICALLY TO PRE-S1 OF HEPATITIS B VIRUS AND USE OF THE ANTIBODY

(71) Applicant: GENEONE LIFE SCIENCE, INC., Seoul (KR)

(72) Inventors: Hyo Jeong Hong, Seoul (KR); Jin Hong Kim, Daejeon (KR)

(73) Assignee: GENEONE LIFE SCIENCE, INC., Seoul (KR)

(*) Notice: Subject to any disclaimer, the term of this patent is extended or adjusted under 35 U.S.C. 154(b) by 0 days.

(21) Appl. No.: 15/606,087

(22) PCT Filed: Nov. 27, 2015

(86) PCT No.: PCT/KR2015/012837
§ 371 (c)(1),
(2) Date: May 26, 2017

(87) PCT Pub. No.: WO2016/085289
PCT Pub. Date: Jun. 2, 2016

(65) Prior Publication Data
US 2017/0260258 A1  Sep. 14, 2017

(30) Foreign Application Priority Data
Nov. 27, 2014 (KR) .......................... 10-2014-0167371

(51) Int. Cl.
*A61K 39/42* (2006.01)
*C07K 16/08* (2006.01)
*G01N 33/569* (2006.01)

(52) U.S. Cl.
CPC ...... *C07K 16/082* (2013.01); *G01N 33/56983* (2013.01); *C07K 2317/24* (2013.01); *C07K 2317/56* (2013.01); *C07K 2317/565* (2013.01); *C07K 2317/76* (2013.01); *C07K 2317/92* (2013.01); *G01N 2333/02* (2013.01); *G01N 2469/10* (2013.01)

(58) Field of Classification Search
None
See application file for complete search history.

(56) References Cited

U.S. PATENT DOCUMENTS

2006/0014937 A1  1/2006  Kang et al. ................. 530/387.3
2007/0021595 A1  1/2007  Hong ......................... 530/388.15

FOREIGN PATENT DOCUMENTS

KR   10-2007-0099214   10/2007   ............. C07K 16/08
WO   WO 2011-045079    4/2011    ............. C07K 14/02

OTHER PUBLICATIONS

International Search Report (ISR) dated Mar. 8, 2016 in PCT/KR2015/012837, with English translation.
NCBI, GenBank accession No. 2EH7_H dated Nov. 12, 2012.
NCBI, GenBank accession No. 2EH8_L dated Oct. 10, 2012.

*Primary Examiner* — Nianxiang Zou
(74) *Attorney, Agent, or Firm* — Harness, Dickey & Pierce, P.L.C.

(57) ABSTRACT

Provided are: an antibody binding specifically to a surface antigen, pre-S1, of a hepatitis B virus (HBV); a polynucleotide coating the antibody; an expression vector comprising the polynucleotide; a transformation agent comprising the expression vector; and use of the antibody in treating or preventing HBV infection and in detecting an HBV.

25 Claims, 8 Drawing Sheets

Specification includes a Sequence Listing.

FIG. 1

ANTIBODY BINDING SPECIFICALLY TO PRE-S1 OF HEPATITIS B VIRUS AND USE OF THE ANTIBODY

CROSS-REFERENCE TO RELATED APPLICATIONS

This application is a national phase application of PCT Application No. PCT/KR2015/012837, filed on Nov. 27, 2015, which claims the benefit and priority to Korean Patent Application No. 10-2014-0167371, filed Nov. 27, 2014. The entire disclosures of the applications identified in this paragraph are incorporated herein by references.

FIELD

The present invention relates to an antibody binding specifically to a surface antigen, pre-S1, of hepatitis B virus (HBV), a polynucleotide coding for the antibody, an expression vector including the polynucleotide, a transformant including the expression vector, a use of the antibody in preventing or treating HBV infection and a use of the antibody in detecting HBV.

BACKGROUND

Hepatitis B virus (HBV) is a virus with which approximately 240 million people are chronically infected to chronically affect chronic HBV carriers, causing public health problems all over the world. An HBV envelope includes three associated surface glycoproteins, particularly a large (L) protein, a middle (M) protein, and a small (S) protein. These proteins are products which originate from one open reading frame (ORF), and are classified into pre-S1, pre-S2 and S domains. The S protein is encoded in the S domain, and the M protein includes pre-S and S antigens. Also, the L protein includes pre-S1, pre-S2 and S antigens. The three antigens are known to stimulate the production of virus neutralizing antibodies. In particular, the 'a' determinants of the pre-S1 and S antigens against the L protein were reported to play a critical role in virus infection. More specifically, the HBV receptor of liver cells has been identified in recent years. It was found that a protein referred to as a sodium taurocholate transporter (NTCP) is a high-affinity functional receptor that binds to HBV pre-S1 (Yan, H., et al., Sodium taurocholate cotransporting polypeptide is a functional receptor for human hepatitis B and D virus. Elife, 2012. 1: p. e00049). Also, it was found that heparin sulfate proteoglycan (HSPG) is a low-affinity receptor that binds to the a determinant of the S antigen (Sureau, C. and J. Salisse, A conformational heparan sulfate binding site essential to infectivity overlaps with the conserved hepatitis B virus a-determinant. Hepatology, 2013. 57(3): p. 985-94). A region of pre-S1 binding to the NTCP consists of amino acid residues at positions 2 to 47 of an ayw subtype, and consists of amino acid residues at positions 13 to 58 of an adr subtype. These results suggest that the antibody binding to a receptor-binding site of pre-S1 can very effectively serve to inhibit the infection of HBV.

For the immunoprophylaxis of HBV infection, hepatitis B immune globulin (HBIG) prepared from the human anti-HBsAg plasma is administered to infants born from HBsAg-HBeAg-positive parents, susceptible subjects acutely exposed to infectious HBV-containing materials, liver transplant patients having chronic HBV-associated liver diseases, etc. However, HBIG cannot be considered to be an ideal source for antibodies since it exhibits limited obtainability and poor specific activity. In this circumstance, the virus-neutralizing monoclonal antibody against the pre-S1 and S antigens may be an effective substitute for the immunoprophylaxis of HBV infection. Based on this situation, the present inventors have developed a humanized antibody through the grafting of murine monoclonal antibodies KR127 and CDR that recognize amino acid residues (NSNNPDWDF) (this sequence corresponds to $26^{th}$ to $34^{th}$ amino acid residues of the ayw subtype) of HBV pre-S1 of the adr subtype (Korean Registered Patent No. 10-0345463). However, since the humanized antibody has a relatively low antigen-binding affinity and includes a considerable number of amino acid residues derived from a mouse, there has been a lasting demand for development of antibodies that have an effect of inducing an effective neutralization reaction to pre-S1 antigens and simultaneously exhibit lower immunogenicity in humans.

In the last 30 years, monoclonal antibodies (mAbs) have emerged as a potent therapeutic agent in humans with advances in antibody engineering technology. Since non-human antibodies may stimulate an immune response in humans, their therapeutic use has been restricted. To solve these problems, the humanized antibodies have been prepared using the CDR grafting technology of engrafting a complementarity-determining region (CDR) of a murine antibody into a human framework region (FR). However, since some FR residues come in direct contact with antigens or serve to hold a CDR loop structure, the simple CDR grafting often reduces affinity. Therefore, the humanized antibody should be usually prepared using methods other than the CDR grafting to preserve some murine FR residues. However, such a humanized antibody generally induces an immune response in humans at a lower level, compared to the chimeric antibodies, but still exhibits immunogenicity since the CDR is not derived from a human being. Accordingly, there is a demand for development of antibodies capable of minimizing immunogenicity of the humanized antibody while maintaining the affinity to antigens.

DISCLOSURE OF INVENTION

Technical Problem

The present inventors have endeavored to develop antibodies having an excellent binding ability with respect to a pre-S1 protein of HBV and simultaneously exhibiting low immunogenicity in the human body, developed two types of antibodies having a higher HBV neutralizing activity and lower immunogenicity, compared to the antibodies against the conventional pre-S1 antigens, and found that the antibodies may be used as antibody-based therapeutic agents for HBV, and may also be used in the field of immunoprophylaxis of HBV infection. Therefore, the present invention has been completed based on these facts.

Technical Solution

Therefore, it is an aspect of the present invention to provide an antibody binding specifically to a surface antigen, pre-S1, of a hepatitis B virus (HBV).

It is another aspect of the present invention to provide a polynucleotide coding for the antibody, an expression vector including the polynucleotide, and a transformant including the expression vector.

It is still another aspect of the present invention to provide a composition including the antibody.

It is yet another aspect of the present invention to provide a pharmaceutical composition for preventing or treating HBV infection, which includes the antibody.

It is yet another aspect of the present invention to provide a method of preventing or treating HBV infection, which includes administering the antibody to a subject suspected to have HBV infection.

It is yet another aspect of the present invention to provide a use of the antibody in use for the manufacture of medicines for preventing or treating HBV infection.

It is yet another aspect of the present invention to provide a method of providing information for diagnosis of hepatitis B virus (HBV) infection or a method of diagnosing HBV infection, which includes detecting a pre-S1 protein, which is present in a biological sample isolated from a subject suspected to have the HBV infection, through an antigen-antibody reaction using the antibody.

It is yet another aspect of the present invention to provide a composition for detecting HBV, which includes the antibody.

It is yet another aspect of the present invention to provide a kit for detecting HBV, which includes the composition for detecting HBV.

It is yet another aspect of the present invention to provide a use of the antibody in use for preparation of the composition for detecting HBV.

Advantageous Effects

The antibody according to the present invention has a high affinity to pre-S1 and simultaneously exhibits low immunogenicity in the human body, and thus can be useful in the fields requiring the neutralization of HBV.

BRIEF DESCRIPTION OF DRAWINGS

FIG. 1 is a diagram showing amino acid sequences of heavy-chain variable regions (VHs) and light-chain variable regions (VLs) of a murine antibody (i.e., a KR127 antibody) and humanized antibodies (HzKR127 (heavy chain: SEQ ID NO. 33; light chain: SEQ ID NO. 38), HzKR127-3 (heavy chain: SEQ ID NO. 34; light chain: SEQ ID NO: 39), HzKR127-3.1 (SEQ ID NO: 35), and HzKR127-3.2 SEQ ID NO: 36)) (A-VH, B-VL). DP7 (SEQ ID NO: 32) and DPK12 (SEQ ID NO: 37) represent human Ig VH and Vκ germline segments, respectively. The symbol "-"represents the same amino acid residue.

A sequence of the heavy-chain variable region of the KR127 antibody was set forth in SEQ ID NO: 15, a sequence of the light-chain variable region was set forth in SEQ ID NO: 16, and a heavy chain FR1, a heavy chain CDR1, a heavy chain FR2, a heavy chain CDR2, a heavy chain FR3, a heavy chain CDR3, a heavy chain FR4, a light chain FR1, a light chain CDR1, a light chain FR2, a light chain CDR2, a light chain FR3, a light chain CDR3, and a light chain FR4 are set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14, respectively.

Figure 2:
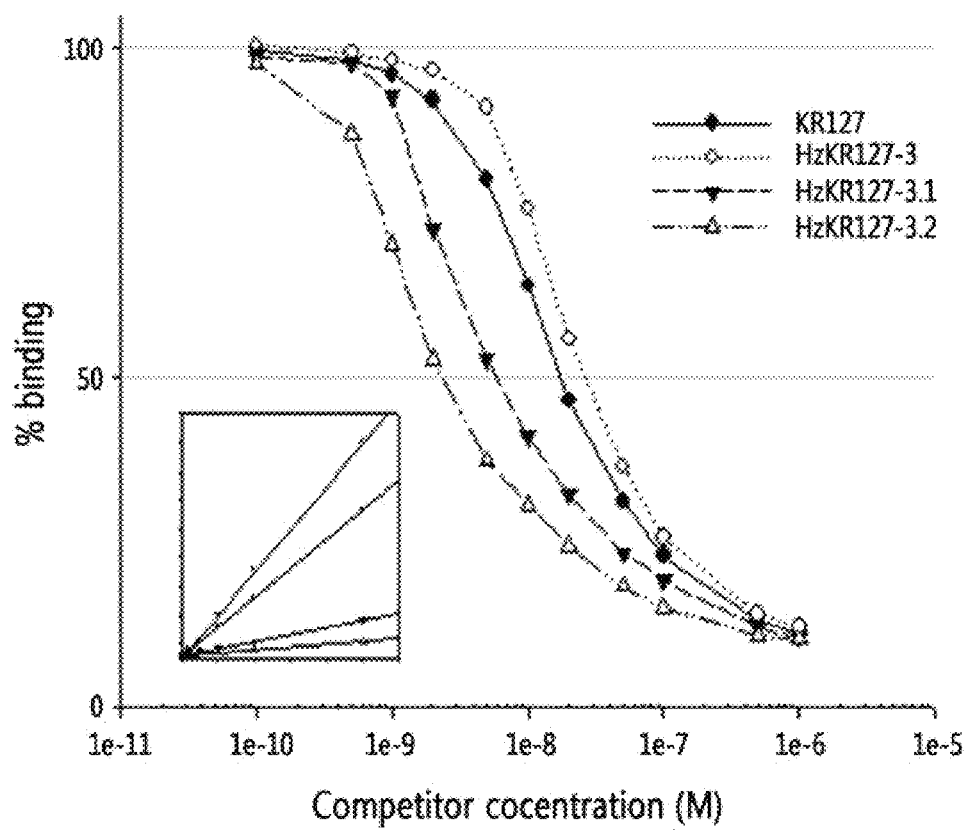
Figure 3A:
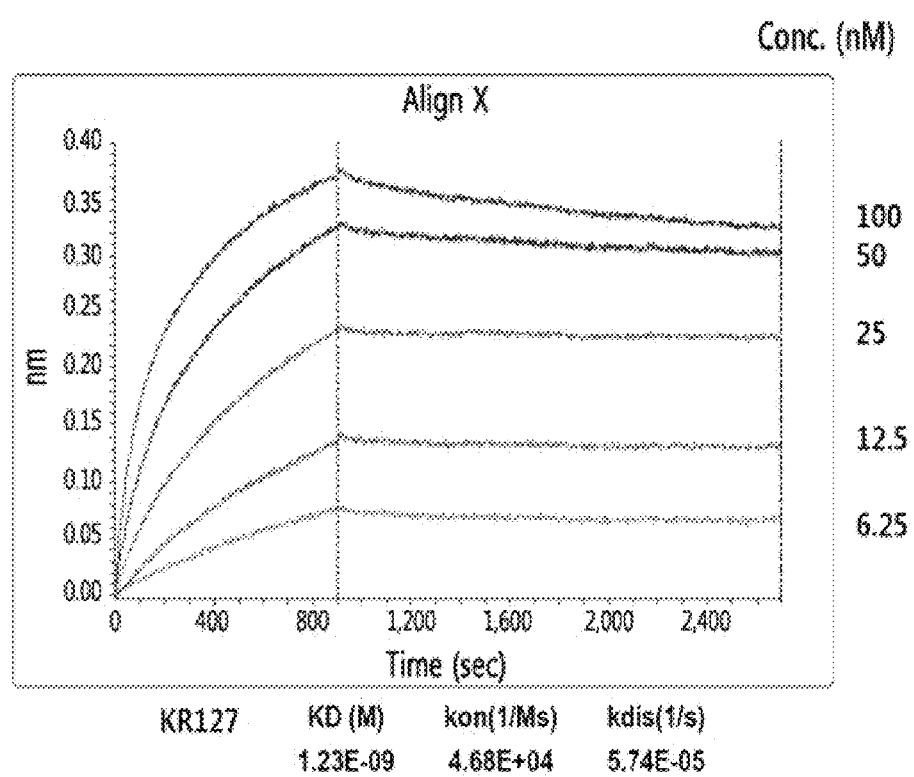
Figure 3B:
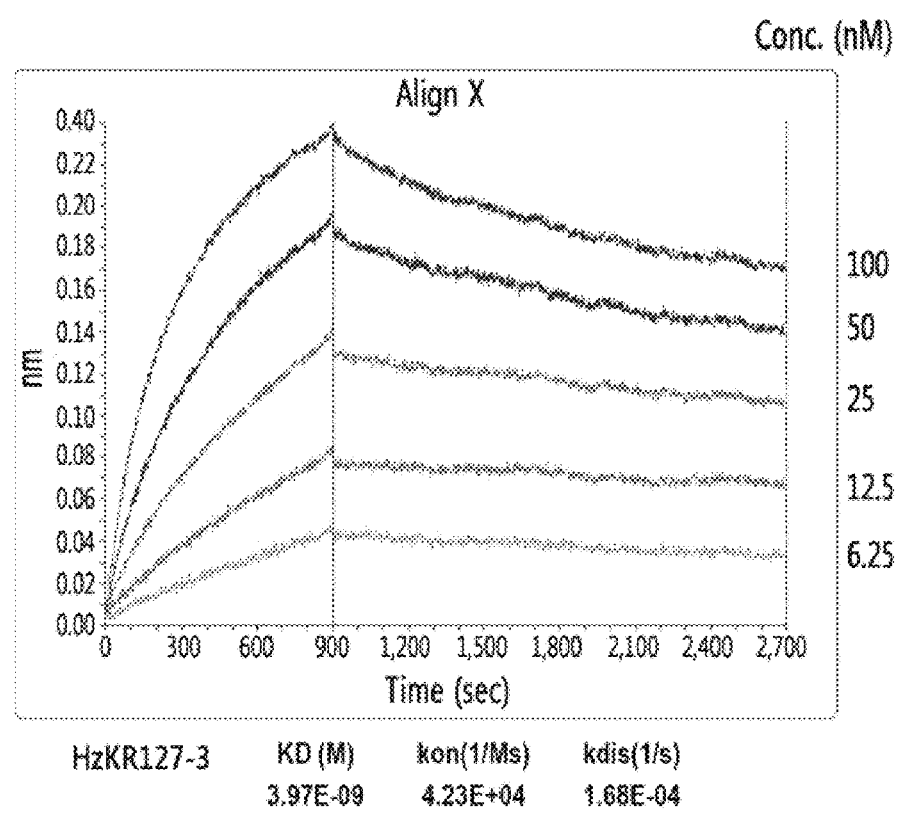
Figure 3C:
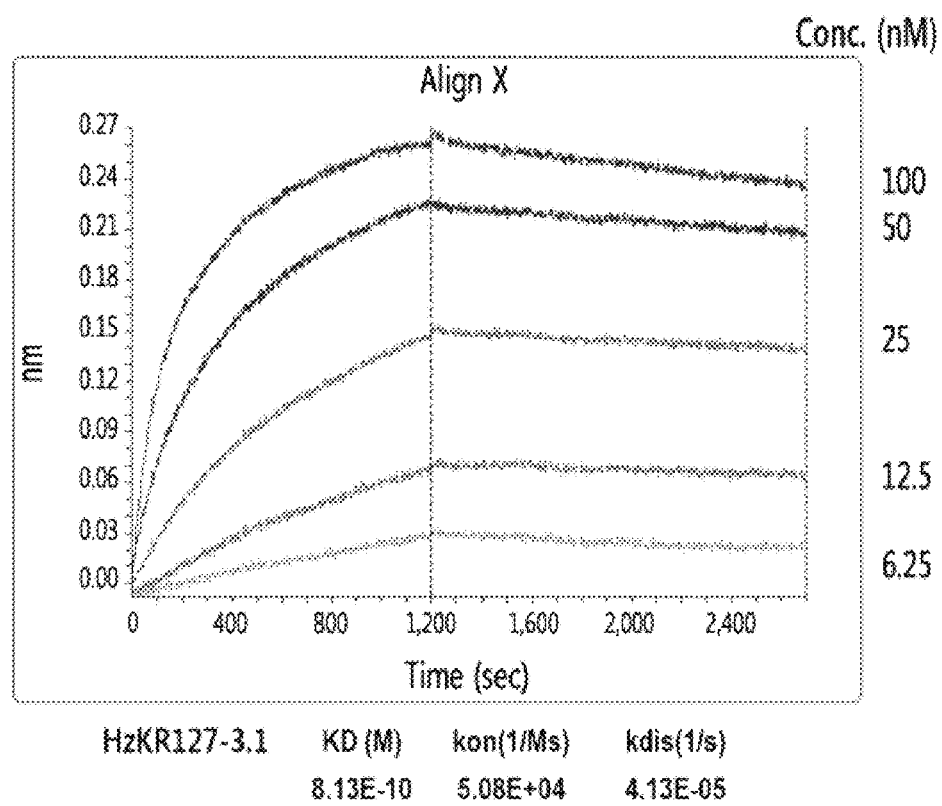
Figure 3D:
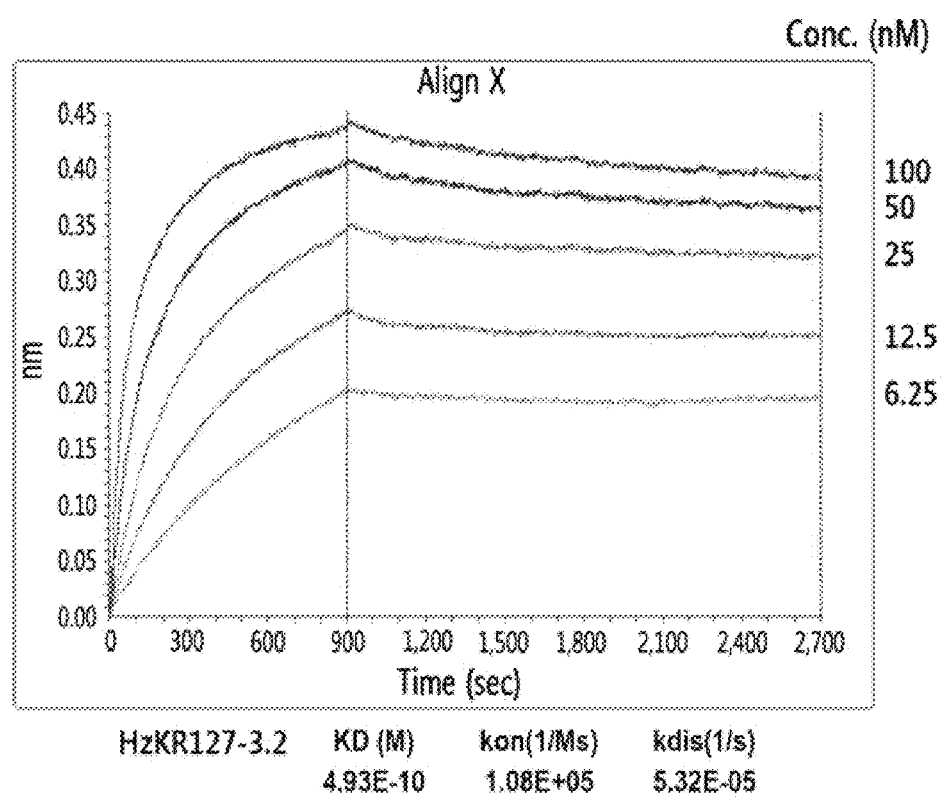

FIG. 2 is a diagram showing the results of determining the affinities of antibodies using a competitive ELISA method.

FIGS. 3A to 3D are diagrams showing the results of determining the affinities of KR127, HzKR127, HzKR127-3.1 and HzKR127-3.2 antibodies using an Octet Red system.

Figure 4:
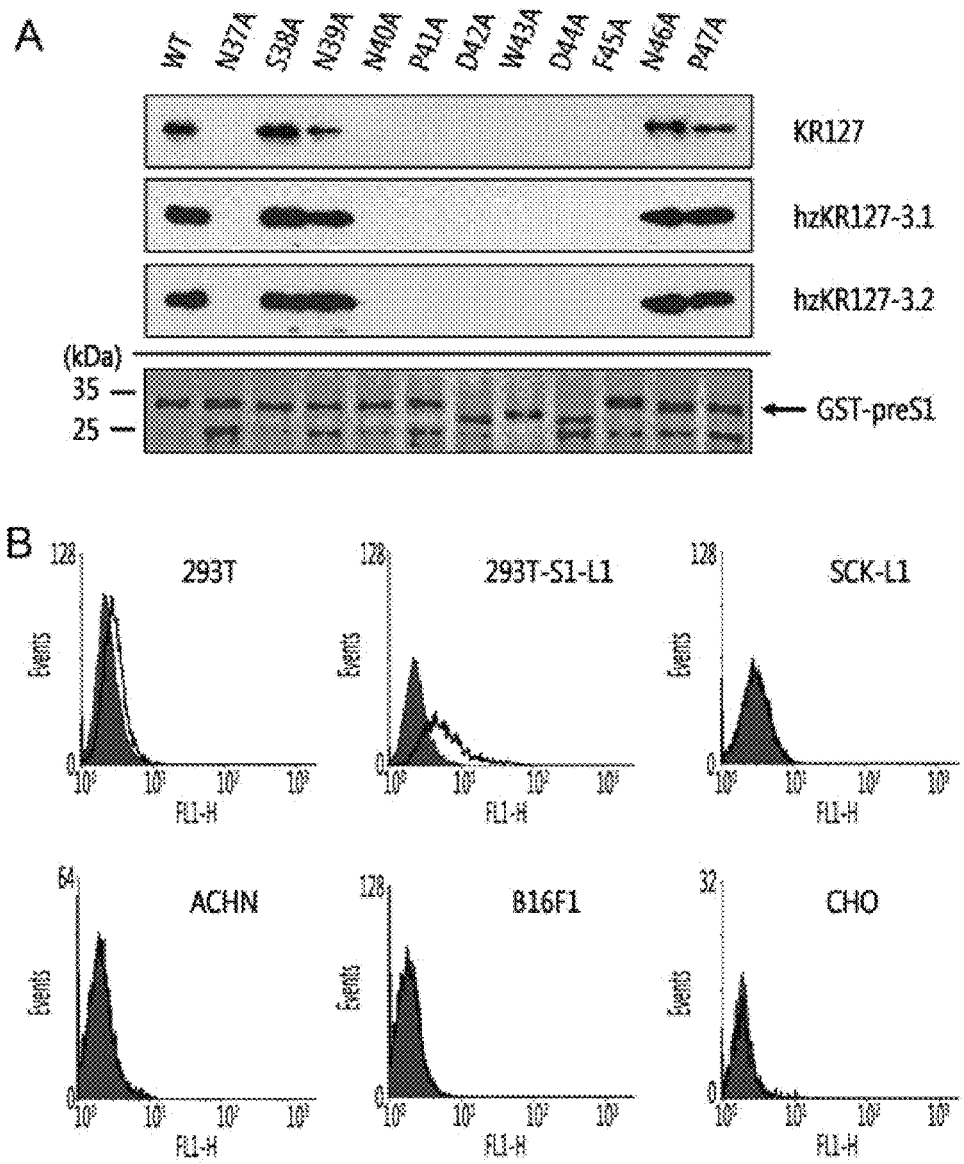

FIG. 4 is a diagram showing the results of determining the epitope specificity (A) and off-target activity (B) of HzKR127-3.2.

(A) A wild-type GST-pre-S1 ($1^{st}$ to $56^{th}$ amino acids) protein and alanine-substituted mutants thereof were expressed in Escherichia coli (E. coli), subjected to 12% SDS-PAGE, and then Western blotted using a KR127, HzKR127-3.1, or HzKR127-3.2 antibody. A protein band corresponding to the GST-pre-S1 is indicated.

(B) This shows the results obtained by subjecting HzKR127-3.2 to flow cytometry using HEK293T cells (293T-S1-L1) expressing pre-S1 and pre-S1-negative cells (HEK293T, SCK-L1, ACHN, B16F1, and CHO).

Figure 5:
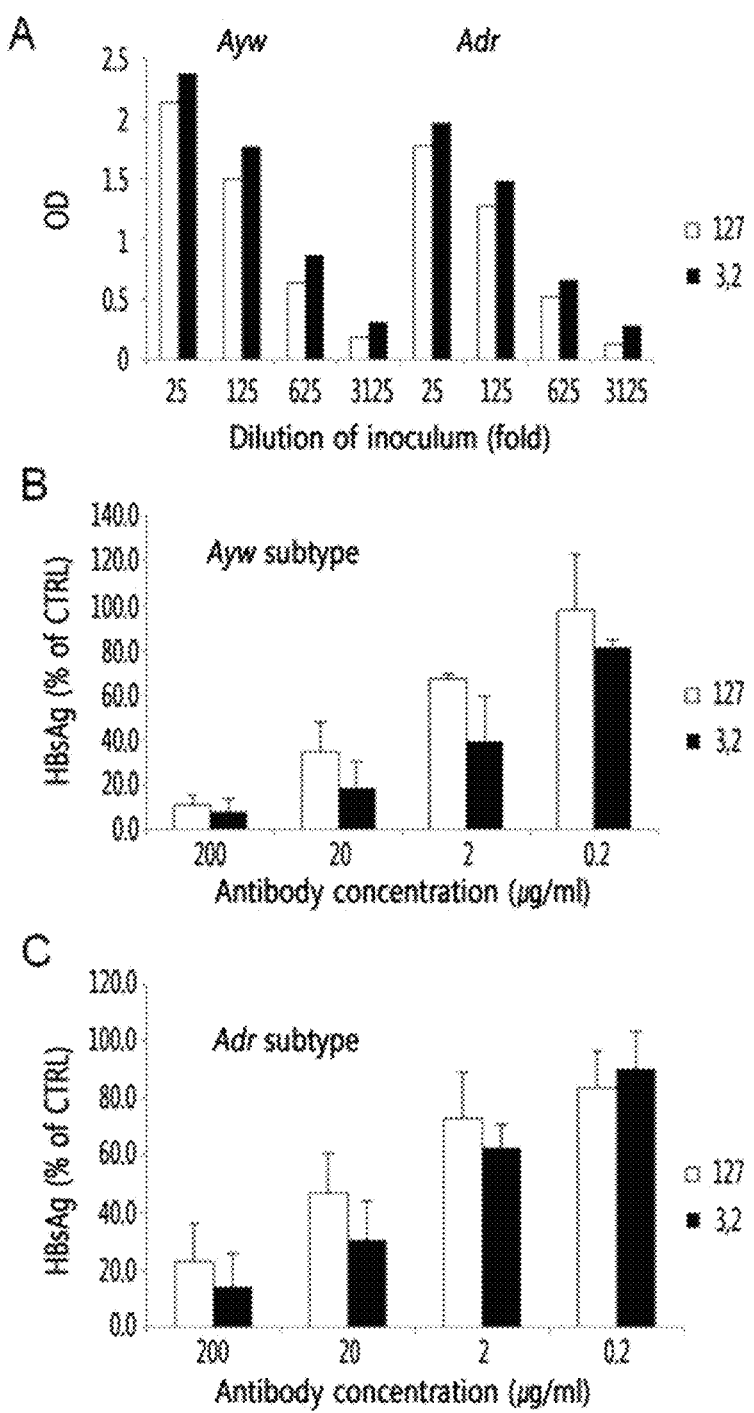

FIG. 5 is a diagram showing the results of measuring in vitro HBV neutralizing activities of HzKR127-3.2 to (A) ayw and (B) adr subtypes of HBV. At a time point of 10 days after infection, HBsAg of a cell culture supernatant was quantified using ELISA, and expressed in percent with respect to the control.

BEST MODE

To achieve the aforementioned objects, one aspect of the present invention provides an antibody binding specifically to a surface antigen, pre-S1, of hepatitis B virus (HBV).

In the present invention, the term "antibody binding specifically to a surface antigen, pre-S1, of hepatitis B virus (HBV)" refers to an antibody that may bind to a surface antigen, pre-S1, of HBV to exhibit a neutralizing activity against HBV.

Specifically, the antibody is an antibody binding specifically to a surface antigen, pre-S1, of HBV, which includes a heavy-chain variable region including a heavy chain CDR1 set forth in SEQ ID NO: 2; a heavy chain CDR2 set forth in SEQ ID NO: 24; and a heavy chain CDR3 set forth in SEQ ID NO: 21, and a light-chain variable region including a light chain CDR1 set forth in SEQ ID NO: 9; a light chain CDR2 set forth in SEQ ID NO: 27; and a light chain CDR3 set forth in SEQ ID NO: 13. More specifically, the antibody may be an antibody including a heavy-chain variable region set forth in SEQ ID NO: 30 and a light-chain variable region set forth in SEQ ID NO: 31.

According to one exemplary embodiment of the present invention, the antibody including the sequences is named HzKR127-3.2. In the present invention, when an Asn residue at a position 58 of HCDR2 of HzKR127-3 is replaced with serine, and an Asp residue at a position 97 of HCDR3 is replaced with alanine, the HzKR127-3 exhibits a remarkably increased affinity to pre-S1 even when only two amino acids mutated. Specifically, it is confirmed that the antibody has an affinity to pre-S1 2.5 times higher than KR127, and also exhibits an excellent in vitro virus neutralizing activity against both of the adr and ayw subtypes of HBV. Also, it is revealed that the in vitro virus neutralizing activity stems from a high binding rate of the antibody to antigens. Since the HzKR127-3.2 antibody also has a characteristic of showing a remarkably reduced potential immunogenicity, compared to the KR127 antibody, the HzKR127-3.2 antibody may have a probability of causing immunogenicity and also exhibit excellent neutralizing activity against HBV when administered to human beings (FIGS. 2 to 5).

Specifically, the antibody may also be an antibody that includes a heavy-chain variable region set forth in SEQ ID NO: 23 and a light-chain variable region set forth in SEQ ID NO: 31.

According to one exemplary embodiment of the present invention, the antibody including the sequences is named HzKR127-3.1. The HzKR127-3.1 may exhibit lower immunogenicity in humans than the KR127 antibody and also has a higher affinity to antigens than the parent antibodies KR127 and HzKR127-3 when a number of residues including FR residues of the KR127 antibody are replaced with residues of a human (FIGS. 2 and 3).

Since such a pre-S1-binding antibody of the present invention may provide higher affinity and lower immunogenicity than the conventional antibodies to exhibit excellent neutralizing activity against HBV, the antibody of the present invention may be used in any applications effectively utilizing the recognition of antigens by the pre-S1.

In the present invention, the term "antibody" refers to a protein molecule that plays a role as a receptor specifically recognizing certain antigens, and includes an immunoglobulin molecule which is immunologically reactive to the antigens. In this case, the antibody includes all types of a polyclonal antibody, a monoclonal antibody, a whole antibody, and an antibody fragment thereof. Also, the term includes a chimeric antibody, a humanized antibody, a human antibody, a bivalent or dual-specific molecule (for example, a dual-specific antibody), a diabody, a triabody, and a tetrabody. The term further includes a single-chain antibody (scAb) retaining a function of binding to FcRn, derivatives of a constant region of the antibody, and an artificial antibody based on the protein scaffold. The whole antibody has a structure including two full-length light chains and two full-length heavy chains. In this case, the light chains are bound to the heavy chain via a disulfide bond, respectively. The whole antibody includes IgA, IgD, IgE, IgM, and IgG, and the IgG includes four subtypes, that is, IgG1, IgG2, IgG3, and IgG4. The antibody fragment refers to a fragment that retains an antigen-binding function, and includes Fd, Fab, Fab', F(ab')2, a variable fragment (Fv), etc. The Fd refers to a heavy chain region included in the Fab fragment. The Fab has a structure including variable regions of light and heavy chains, a constant region of the light chain, and a first constant region (a CH1 domain) of the heavy chain, and thus has one antigen-binding site. The Fab' differs from the Fab in that the Fab' has a hinge region including one or more cysteine residues at the C terminus of the CH1 domain of the heavy chain. An F(ab')2 antibody is generated as a disulfide bond is formed between the cysteine residues in the hinge region of Fab'. The Fv refers to a minimal antibody fragment having only a heavy chain variable region and a light chain variable region. A double-disulfide Fv (dsFv) has a heavy chain variable region and a light chain variable region bound via a disulfide bond, and a single-chain Fv (scFv) generally has a variable region of the heavy chain and a variable region of the light chain covalently via a peptide linker. Such an antibody fragment may be obtained using a protease (for example, an Fab fragment may be obtained when the whole antibody is digested with papain, and an F(ab')2 fragment may be obtained when the whole antibody is digested with pepsin). Preferably, the antibody fragment may be manufactured by means of genetic recombination technology.

In the present invention, the term "monoclonal antibody" refers to an antibody molecule having a single molecular composition obtained from substantially the same population of antibodies. Such a monoclonal antibody exhibits single binding specificity and affinity with respect to a certain epitope In the present invention, the term "chimeric antibody" refers to an antibody formed by recombining a variable region of a murine antibody and a constant region of a human antibody by means of recombinant DNA technology. In this case, the chimeric antibody may be clinically used because an immune response of the chimeric antibody is highly improved, compared to the murine antibody.

Typically, an immunoglobulin has a heavy chain and a light chain. In this case, each of the heavy chain and the light chain includes a constant region and a variable region (each region is also known as a domain). Each of the variable regions of the light chain and the heavy chain includes three hypervariable regions referred to as complementarity-determining regions (hereinafter referred to as "CDRs"), and four framework regions. In general, the CDR serves to bind to an epitope of an antigen. Typically, the CDRs of each chain are sequentially referred to as CDR1, CDR2, and CDR3, starting from the N termius thereof. Also, the CDRs are referred to as heavy chain CDR1, heavy chain CDR2, and heavy chain CDR3 when the CDRs are positioned on the heavy chain, and referred to as light chain CDR1, light chain CDR2, and light chain CDR3 when the CDRs are positioned on the light chain.

Also, when the aforementioned antibody of the present invention includes a constant region, the antibody may include a constant region derived from IgG, IgA, IgD, IgE, IgM, or a combination or hybrid thereof.

In the present invention, the term "combination" means that a polypeptide encoding a single-chain immunoglobulin constant region from the same origin is combined with a single-chain polypeptide from another origin different from the origin so as to form a dimer or a multimer. For example, a dimer or a multimer may be formed from two or more constant regions selected from the group consisting of constant regions of IgG, IgA, IgD, IgE, and IgM.

In the present invention, the term "constant region derived from a hybrid" means that a heavy-chain constant region of a single-chain immunoglobulin includes all types of sequences derived from two or more heavy-chain constant regions of the immunoglobulin, particularly two or more heavy-chain constant regions of the immunoglobulin selected from IgG, IgA, IgD, IgE, and IgM.

For example, it is possible for a hybrid of domains to include 1 to 4 domains selected from the group consisting of CH1, CH2, CH3 and CH4 of IgG, IgA, IgD, IgE and IgM.

In the present invention, the antibody may be preferably a humanized antibody, but the present invention is not limited thereto.

In the present invention, the term "humanized antibody" refers to an antibody formed by grafting all or some of a CDR sequence of a murine monoclonal antibody into a human antibody. For example, CDRs of a murine monoclonal antibody may be recombined with human antibody-derived FR to prepare a humanized variable region, and the humanized variable region may be recombined with a constant region of a desired human antibody to prepare a humanized antibody, but the present invention is not limited thereto. Also, when only the mouse-derived CDRs are engrafted, the affinity of the humanized antibody may be degraded. Therefore, the affinity may be enhanced by replacing amino acid residues of the FR with amino acids of the murine antibody, but the present invention is not limited thereto.

Another aspect of the present invention provides a polynucleotide coding for the antibody, an expression vector including the polynucleotide, and a non-human transformant including the expression vector.

The antibody is as described above.

The expression vector including the polynucleotide which codes for the antibody provided in the present invention is not particularly limited, but may become a vector which may replicate and/or express the polynucleotide in eukaryotic or prokaryotic cells including mammalian cells (for example, human, monkey, rabbit, rat, hamster, mouse cells, etc.), plant cells, yeast cells, insect cells, or bacterial cells (for example, *E. coli*, etc.), may be preferably operably linked to a proper promoter so that the nucleotide can be expressed in a host cell, and may also become a vector including at least one selective marker. For example, the expression vector may have a shape in which the polynucleotide is introduced into a phage, a plasmid, a cosmid, a mini-chromosome, a viral or retroviral vector, etc.

The expression vector including the polynucleotide coding for the antibody may be an expression vector including a polynucleotide coding for either a heavy chain or light chain of the antibody, or an expression vector including both polynucleotides coding for the heavy chain and the light chain.

The transformant into which the expression vector provided in the present invention is introduced is not particularly limited, but may include bacterial cells, such as *E. coli, Streptomyces* sp., *Salmonella typhimurium*, etc., which are transformed through introduction of the expression vector; yeast cells; fungal cells such as *Pichia pastoris*, etc.; insect cells such as *Drosophila* sp., *Spodoptera* Sf9 cells, etc.; animal cells such as Chinese hamster ovary cells (CHO), SP2/0 (mouse myeloma), human lymphoblastoid cells, COS, NSO (mouse myeloma), 293T, Bowes melanoma cells, HT-1080, BHK (baby hamster kidney cells), HEK (human embryonic kidney cells), PERC.6 (human retinal cells), etc.; or plant cells.

In the present invention, the term "introduction" refers to a method of transferring a vector including a polynucleotide coding for the antibody to a host cell. Such introduction may be performed using various methods known in the related art, such as a calcium phosphate-DNA co-precipitation method, a DEAE-dextran-mediated transfection method, a polybrene-mediated transfection method, an electroporation method, a microinjection method, a liposome fusion method, Lipofectamine and protoplast fusion methods, etc. Also, the term "transduction" means that a target substance is transferred into cells by means of infection using viral particles. In addition, the vector may be introduced into a host cell through gene bombardment, etc. In the present invention, the introduction may be used interchangeably with the transformation.

Still another aspect of the present invention provides a composition including the antibody.

The antibody is as described above.

Specifically, the composition may be in the form of a pharmaceutical composition.

More specifically, the composition may be a pharmaceutical composition for preventing or treating HBV infection, which include the antibody. In this case, the composition may be used to prevent or treat hepatitis B.

In the present invention, the term "hepatitis B" refers to a disease in which inflammation is caused in the liver due to an immune response when the liver cells are infected with HBV. The antibody of the present invention may be used to prevent or treat hepatitis B because the antibody has excellent neutralizing capacity against HBV.

In the present invention, the term "prevention" may refer to all types of actions in which the composition is administered to suppress or delay the onset of HBV infection, and the "treatment" may refer to all types of actions in which the composition is administered to improve or benefit the symptoms caused by the HBV infection.

The pharmaceutical composition may further include a pharmaceutically acceptable carrier.

In the present invention, the term "pharmaceutically acceptable carrier" refers to a carrier or diluent that does not hinder biological activities and characteristics of a compound administered without stimulating an organism. For the composition prepared into a liquid solution, the pharmaceutically acceptable carrier is sterilized or biocompatible. Thus, saline, sterile water, Ringer's solution, buffered saline, an albumin injection solution, a dextrose solution, a maltodextrin solution, glycerol, ethanol, and a mixture of one or more types thereof may be used as the pharmaceutically acceptable carrier. When necessary, other conventional additives such as an antioxidant, a buffer, a bacteriostatic agent, and the like may be added. Also, after a diluent, a dispersing agent, a surfactant, a binder and a lubricant is additionally added to the composition, the composition may be prepared into an injectable formulation such as an aqueous solution, a suspension, an emulsion, and the like, a pill, a capsule, a granule, or a tablet The pharmaceutical composition may include various oral or parenteral formulations. When prepared, the composition may be prepared using a diluent or an excipient that is generally used in the art, such as a filler, an extending agent, a binder, a wetting agent, a disintegrating agent, a surfactant, etc. A solid preparation for oral administration includes a tablet, a pill, a powder, a granule, a capsule, etc. Such a solid preparation is prepared by mixing at least one excipient, for example, starch, calcium carbonate, sucrose, or lactose, gelatin, with one or more compounds. Also, in addition to the simple excipient, lubricants such as magnesium stearate, talc, and the like are used. A liquid preparation for oral administration includes a suspension, a liquid for internal use, an emulsion, a syrup, etc. In addition to simple diluents generally used in the art, for example, water, liquid paraffin, and the like, the liquid preparation may include various excipients, for example, a wetting agent, a sweetening agent, an air freshener, a preservative, etc. The preparation for parenteral administration includes sterilized aqueous solution, a non-aqueous solvent, a suspension, an emulsion, a lyophilized preparation, a suppository, etc. Propylene glycol, polyethylene glycol, a vegetable oil such as olive oil, an injectable ester such as ethyl oleate, and the like may be used as a non-aqueous solvent or a suspending agent. Witepsol, Macrogol, Tween 61, cacao butter, laurin butter, glycerogelatin, and the like may be used as a base for suppositories.

The pharmaceutical composition may have one formulation selected from the group consisting of a tablet, a pill, a powder, a granule, a capsule, a suspending agent, a liquid for internal use, an emulsifying agent, a syrup, a sterilized aqueous solution, a non-aqueous solvent, a suspension, an emulsion, a lyophilized preparation, and a suppository.

The composition of the present invention is administered at a pharmaceutically effective amount.

In the present invention, the term "pharmaceutically effective amount" refers to an amount sufficient to treat a disease at a reasonable benefit/risk ratio applicable to any medical treatment. In this case, a level of the effective dose may be determined depending on the type, severity, age, and sex of a subject, the type of cancer, the activity of a drug, the sensitivity to the drug, an administration time, a route of administration, and a secretion rate, a therapeutic period, factors including drugs to be used together, and other factors well known in the field of medicine. The composition of the present invention may be administered as an individual therapeutic agent, or may be administered in combination with other therapeutic agents. In this case, the composition may be administered sequentially or concurrently with conventional therapeutic agents. And, the composition of the present invention may be administered in a single dose or a multiple dose. By considering all the above factors, it is important to administer the composition at a dose in which the maximum effect can be achieved without any side effects when administered at a minimum dose. Thus, the dose of the composition may be easily determined by those skilled in the related art.

Specifically, the composition may also be a composition for detection of HBV. The composition may also be used as a composition for diagnosis of hepatitis B.

Yet another aspect of the present invention provide a method of preventing or treating HBV infection, which includes administering the antibody to a subject suspected to have the HBV infection. The method may also be used to prevent or treat hepatitis B.

The method may be a method of preventing or treating HBV infection, which includes administering the pharmaceutical composition further including an antibody and a pharmaceutically acceptable carrier to a subject who is infected with HBV or likely to be infected with HBV. Here, the pharmaceutically acceptable carrier is as described above.

The subject includes a mammal such as cattle, a pig, sheep, a chicken, a dog, a human, and the like, a bird, etc. In this case, subjects whose HBV infection is treated by administering the composition of the present invention are included in the subject without limitation.

In this case, the antibody may be administered at pharmaceutically effective amount in a single dose or a multiple dose. In this case, the antibody may be administered in the form of a liquid, a powder, an aerosol, a capsule, an enteric-coated tablet or capsule, or a suppository. The route of administration includes intraperitoneal administration, intravenous administration, intramuscular administration, subcutaneous administration, endothelial administration, oral administration, topical administration, intranasal administration, intrapulmonary administration, intrarectal administration, etc., but the present invention is not limited thereto. However, because proteins or peptides are digested upon oral administration, an oral composition may be formulated to coat an active drug or protect the active drug from being decomposed in the stomach. Also, the pharmaceutical composition may be administered using any device for delivering an active material into target cells.

Yet another aspect of the present invention provides a use of the antibody in use for the manufacture of medicines for preventing or treating HBV infection. The medicines may also be used to prevent or treat hepatitis B.

The antibody and the prevention or treatment of HBV infection are as described above.

Yet another aspect of the present invention provides a method of providing information for diagnosis of HBV infection, which includes detecting a pre-S1 protein, which is present in a biological sample isolated from a subject suspected to have HBV infection, through an antigen-antibody reaction using the antibody. Also, the method may be a method of diagnosing HBV infection.

The antibody and the HBV are as described above.

Also, the method may be used to diagnose hepatitis B.

In the method of providing information for diagnosis of HBV infection, the pre-S1 protein may be detected by allowing the pre-S1-specific antibody of the present invention to react with a biological sample isolated from a subject suspected to have HBV infection and detecting formation of an antigen-antibody complex. In this way, the information for diagnosis of HBV infection may be provided.

Specifically, the method may be a method that includes (a) treating a biological sample isolated from a subject suspected to have HBV infection with the antibody to detect a pre-S1 protein through an antigen-antibody reaction; and (b) diagnosing the subject as a HBV-infected patient when a level of the pre-S1 protein detected in the step (a) is higher than that of the control after the level of the pre-S1 protein is compared to the control.

In the present invention, the term "biological sample" may include tissues, cells, whole blood, serum, tissue autopsy samples (brain, skin, lymph node, spinal cord, etc.), a cell culture supernatant, destroyed eukaryotic cells, bacterial expression systems, etc., but the present invention is not limited thereto. The presence of the pre-S1 protein and the HBV infection may be determined by allowing these biological samples in an engineered or non-engineered state to react with the antibody of the present invention.

In the present invention, the term "antigen-antibody complex" refers to a conjugate of a pre-S1 protein antigen in a sample and the antibody according to the present invention that recognizes the pre-S1 protein antigen. The formation of such an antigen-antibody complex may be detected using any method selected from the group consisting of a colorimetric method, an electrochemical method, a fluorimetric method, luminometry, a particle counting method, visual assessment, and a scintillation counting method. However, such methods are not particularly limited, and may be widely applied to various fields.

In the present invention, various labels may be used to detect the antigen-antibody complex. Specific examples of the labels may be selected from the group consisting of an enzyme, a fluorescent material, a ligand, a luminous material, microparticles, a radioactive isotope, etc., but the present invention is not particularly limited thereto.

The enzyme used as the detection label includes achetylcholinesterase, alkaline phosphatase, β-D-galactosidase, horseradish peroxidase, β-lactamase, etc., the fluorescent material includes fluorescein, $Eu^{3+}$, an $Eu^{3+}$ chelate, cryptate, etc., the ligand includes biotin derivatives, etc., the luminous material includes acridinium ester, isoluminol derivatives, etc., the microparticles include colloidal gold, colored latex, etc., and the radioactive isotope includes $^{57}Co$, $^{3}H$, $^{125}I$, $^{125}I$-Bonton Hunter reagents, etc.

Preferably, the antigen-antibody complex may be detected using an enzyme-linked immunosorbent assay (ELISA). The enzyme-linked immunosorbent assay (ELISA) includes various ELISA methods such as a direct ELISA using a labeled antibody recognizing antigens attached to a solid support, an indirect ELISA using a labeled secondary antibody recognizing a capture antibody in a complex of antibodies recognizing antigens attached to a solid support, a direct sandwich ELISA using another labeled antibody recognizing antigens in a complex of antibody and antigen attached to a solid support, an indirect sandwich ELISA using a labeled secondary antibody reacting with other antibodies recognizing antigens in a complex of antibody and antigen attached to a solid support, followed by recognizing the other antibodies, etc.

The antibody may have a detection label. When the antibody has no detection label, the presence of the antigen-antibody complex may be determined by treating the antibody with another antibody which may capture these monoclonal antibodies and has a detection label.

Yet another aspect of the present invention provides a kit for detecting HBV, which includes the composition for detecting HBV. The kit may also be in the form of a kit for diagnosis of hepatitis B.

The composition, the hepatitis B and the diagnosis are as described above.

Yet another aspect of the present invention provides a use of the antibody in use for preparation of the composition for detecting HBV.

The antibody and HBV are as described above.

MODE FOR INVENTION

Hereinafter, the present invention will be described in detail with reference to specific embodiments thereof. However, it should be understood that the embodiments are given by way of illustration only, but not intended to limit or define the scope of the present invention.

EXAMPLE 1

Experiment Method (1) Cell Culture

HEK293T, ACHN, B16F1, and SCK-L1 cells were cultured in DMEM media (Invitrogen) supplemented with 10% fetal bovine serum (FBS). CHO-DG44 cells was cultured in a DMEM/F12 medium (Invitrogen) including hypoxanthine (10 mg/L), thymidine (10 mg/L), glycine (50 mg/L), glutamine (587 mg/L), glucose (4.5 mg/L), 10% FBS, and antibiotic-antifungal agent (GIBCO/BRL). HepaRG cells were cultured and differentiated using a method disclosed by Gripon, P et al. (Proc Natl Acad Sci U S A. 2002 Nov. 26; 99(24): 15655-60.). Thereafter the HepaRG cells were cultured at 37° C. in a 96-well plate containing a William's E medium (Gibco Life technologies) supplemented with 5% fetal bovine serum, 2% DMSO, 5 mg/L insulin, $5 \times 10^{-6}$ M hydrocortisone, 5 μg/L sodium selenite, 20,000 UI/L penicillin, and 20 mg/L streptomycin in a 5% $CO_2$ incubator, and then maintained.

(2) Preparation, Expression and Purification of Humanized Antibody

Humanized VH and VL genes were synthesized by GeneArt (Germany), and then sequentially sub-cloned into EcoRI-ApaI and HindIII-BsiWI sites of pdCMV-dhfrC-cA10A3 containing human $C_{\gamma 1}$ and $C_\kappa$, respectively. The prepared expression vector was introduced into HEK293T cells using Lipofectamine (Invitrogen). A cell culture supernatant was subjected to affinity chromatography using a protein-A sepharose column (Millipore), and a concentration of the protein was determined based on the molar absorptivity using NanoDrop (Thermo Scientific). To check whether the purified protein was maintained intact, the purified protein was analyzed using SDS-PAGE.

(3) Affinity Determination

Affinity determination was carried out using a competitive ELISA, and a specific analytic method was as follows (Oh MS et al., A new epitope tag from hepatitis B virus pre-S1 for immunodetection, localization and affinity purification of recombinant proteins, J Immunol Methods. 2003 December; 283(1-2): 77-89.).

A solution including 5 to 10 ng of an antibody was incubated with various concentrations of a GST-pre-S1 antigen ($10^{-10}$ to $0^{-6}$ M, a competitive antigen) at a temperature of 37° C. for 3 hours, and the resulting reaction mixture was added to each of wells coated with 100 ng of the GST-pre-S1 antigen. The mixture was incubated at 37° C. for an hour, and a goat anti-mouse IgG (Fc-specific)-HRP conjugate (1:5000 v/v, Pierce, Ill.) was added thereto. Then, the resulting mixture was incubated for 30 minutes. The mixture was washed, and a 0.2 M citrate-$PO_4$ buffer (pH 5.0) including 0.04% ortho-phenylenediamine-dihydrochloride (OPD) and 0.012% $H_2O_2$ was then added to each well. The reaction was stopped using 2.5 M $H_2SO_4$, and the optical density (A) was measured at 492 nm using an ELISA reader (SOFTmaxPRO, Molecular Devices, USA). The dissociation equilibrium constant ($K_d$) was analyzed using Klotz plot.

For the affinity determination using Octet Red, an anti-human Fc-coated biosensor tip (ForteBio, 18-0015) was activated for 20 minutes with PBS (0.1% PBA) including bovine serum albumin (0.1% w/v) while stirring a 96-well microplate (Greiner bio-one, 655209) at 100 rpm. Thereafter, the biosensor tip was saturated with 2 μg/mL of the antibody for 10 minutes. This generally resulted in a capture level of 1 nm. The GST-pre-S1 was prepared through the 2-fold serial dilution with 0.1% PBA (6.25, 12.5, 25, 50, and 100 nM), and each was incubated in the tip to which the antibody was bound. The binding and separation rates were measured for 15 minutes and 30 minutes, respectively. In all the measurements, a baseline drift was corrected by subtracting a control sensor exposed to only a running buffer. The operating temperature was maintained at 30° C. The data was analyzed using a 1:1 interaction model (fitting global, Rmax unlinked by sensor) equipped with ForteBio data analysis software 7.0.

(4) Western Blot Analysis

Each of alanine-substituted mutant proteins of GST-pre-S1 ($1^{st}$ to $56^{th}$ amino acids) and pre-S1 ($37^{th}$ to $47^{th}$ amino acids) was expressed in *E. coli* DH5α cells. The protein extracts were subjected to 12% SDS-PAGE and Western blotting using a KR127 antibody or a humanized KR127 antibody (1 μg/mL), and analyzed using an anti-mouse or human IgG (Fc-specific) HRP conjugate (1:5000 v/v, Thermo Scientific).

(5) Flow Cytometric Analysis

Cells were incubated at 4° C. for 60 minutes in 100 μL of PBA including 1 μg of the antibody. The cells were washed three times with PBA, and then incubated with a fluorescein isothiocyanate-conjugated anti-hFc antibody (BD Pharmingen) at 4° C. for 30 minutes. For an antibody binding assay, propidium iodide (PI)-negative cells were analyzed using FACSCalibur (Becton Dickinson).

(6) In Vitro Neutralization Assay

An in vitro HBV infection and neutralization assay was carried out using differentiated HepaRG cells. The differentiated HepaRG cells were seeded at a density of $6 \times 10^4$ cells/well (including 100 μL of a cell culture medium), and then infected with HBV viral particles of an adr or ayw subtype (approximately $10^6$ viral genomic equivalents) for 6 days. For a neutralization assay, the viral particles were pre-incubated with a given concentration of the antibody at room temperature for 30 minutes, and again incubated for 24 hours with the cultured HepaRG cells covered with 100 μL of a culture medium. The infected cells were again washed with the culture broth, and incubated for another 10 days. In this case, the medium was replaced with fresh one once every other day. After 10 days of the infection, the cell culture supernatant was diluted up to 50 folds, and the concentration of HBsAg was measured sing an ELISA kit (Bio-Rad).

EXAMPLE 2

Preparation of Antibody against Pre-S1 of HBV (1) Preparation of HzKR127-3

Figure 1:
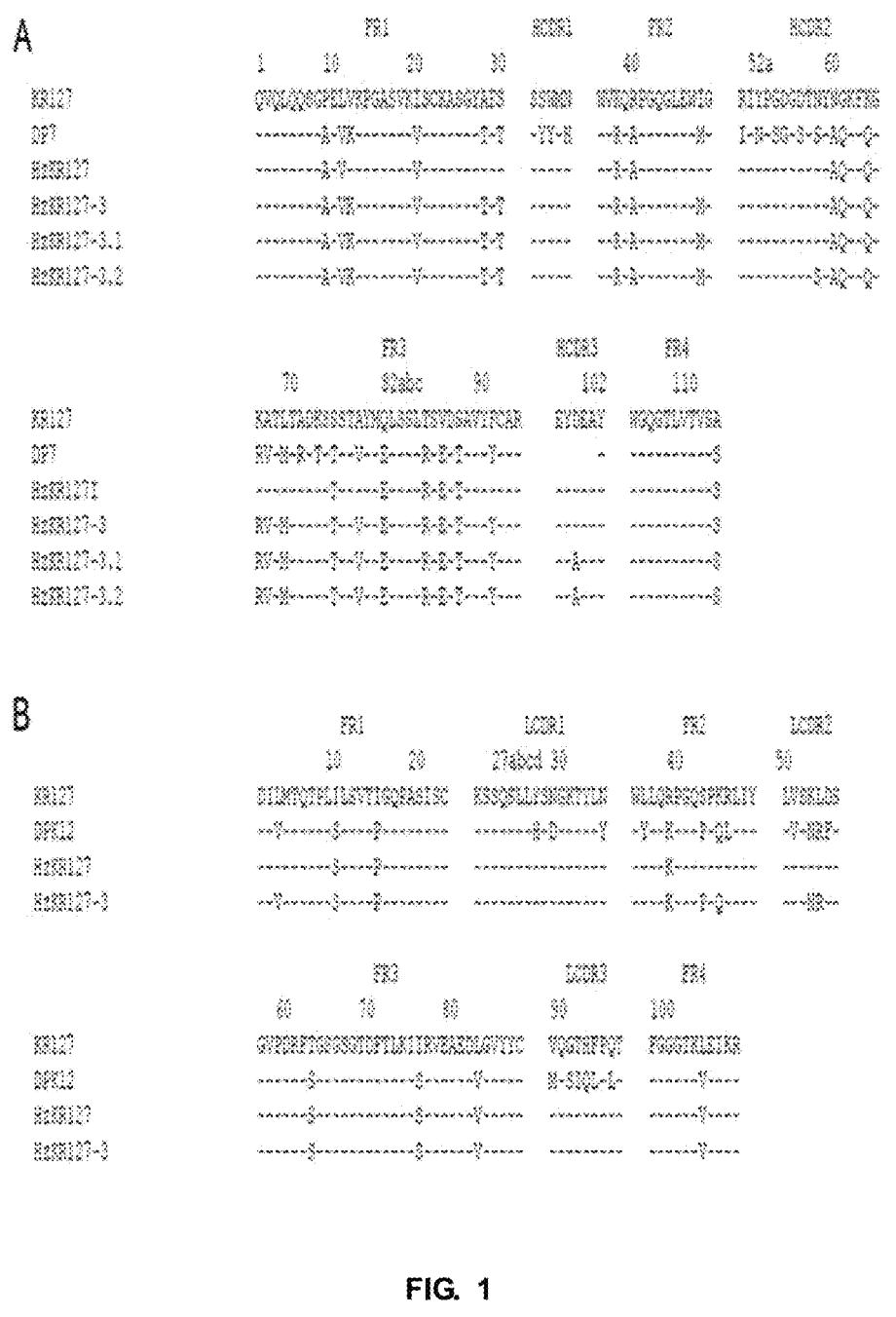

An amino acid sequence of a humanized antibody HzKR127 into which CDRs of murine antibodies KR127 and KR127 were engrafted is shown in FIG. 1 (FIG. 1A shows an amino acid sequence of a heavy-chain variable region (VH), and FIG. 1B shows an amino acid sequence of a light-chain variable region (VL)). Site-directed mutations were carried out to develop antibodies whose immune activities were improved compared to the HzKR127 antibody.

In the case of the VH, nine FR residues (Val12, Ala28, Ser30, Ile48, Lys66, Ala67, Leu69, Ala78, and Phe91; indicated by Kabat numbering) of KR127 were replaced with the corresponding human-derived amino acid residues, as shown in FIG. 1. However, two FR3 residues (Ala71 and Lys73) of the KR127 were conserved intact.

In the case of the VL, three FR residues (Leu3, Ser43, and Lys45) of KR127 were replaced with the corresponding human-derived amino acid residues. However, two FR2 residues (Leu36 and Arg46) of the KR127 were conserved intact. The shape of an antigen-binding pocket was maintained and the optimal binding to antigens was realized by conserving Leu36 intact. Since it was confirmed a 46$^{th}$ amino acid residue was able to stabilize the shape of HCDR3, the amino acid residue was conserved intact.

In addition to the FR residues, two LCDR2 residues (Lys53 and Leu54) were replaced with the corresponding residues of a human sequence.

The humanized VH and VL sequences designed thus were synthesized, and the combined with human $C_{\gamma 1}$ and $C_{\kappa}$, respectively, to prepare expression plasmids, pdCMV-dhfrC-HzKR127-3. The plasmid DNA was introduced into HEK293T cells, and the prepared humanized antibody HzKR127-3 was purified from the cell culture supernatant. The affinity of HzKR127-3 to GST-pre-S1 was determined using a competitive ELISA. As a result, it was revealed that the HzKR127-3 antibody had a somewhat low affinity, compared to the parent antibody KR127 (FIG. 2). The affinity of the HzKR127-3 was determined using Octet Red. As a result, it was revealed that the affinity ($K_D$) of HzKR127-3 was approximately three-folds lower than KR127. It was assayed that such a decline was mainly caused by a rise in dissociation rate (Table 1 and FIGS. 2, 3A and 3B).

TABLE 1

| Antibody name | $K_D$ (M) | $K_{on}$ (1/Ms) | $K_{off}$ (1/s) |
| --- | --- | --- | --- |
| KR127 | $1.23 \times 10^{-9}$ | $4.68 \times 10^4$ | $5.74 \times 10^{-5}$ |
| HzKR127-3 | $3.97 \times 10^{-9}$ | $4.23 \times 10^4$ | $1.68 \times 10^{-4}$ |
| HzKR127-3.1 | $8.13 \times 10^{-10}$ | $5.08 \times 10^4$ | $4.13 \times 10^{-5}$ |
| HzKR127-3.2 | $4.93 \times 10^{-10}$ | $1.08 \times 10^5$ | $5.32 \times 10^{-5}$ |

(2) Preparation of HzKR127-3.1 and HzKR127-3.2

Because the HzKR127-3 had a somewhat low affinity, compared to the KR127, site-directed mutations were carried out on the sequence of the HzKR127-3 so s to enhance the affinity.

Specifically, an antibody named HzKR127-3.1 was prepared by replacing an Asp97 amino acid residue with alanine. Thereafter, the antibody was temporarily expressed in HEK293T cells, and purified, and the affinity was sequentially assayed using a competitive ELISA and Octet Red. As a result, it was revealed that the affinity of the HzKR127-3.1 was $8.13 \times 10^{-10}$ M, the value of which was 4.9 folds higher than that of the HzKR127-3 ($3.97 \times 10^{-9}$ M). Also, the analysis results showed that such a rise in affinity was mainly caused by a decline in dissociation rate (Table 1, FIG. 2 and FIG. 3C).

To further enhance the affinity of the HzKR127-3.1, an antibody named HzKR127-3.2 was prepared by replacing an Asn amino acid residue at a position 58 of HCDR2 of the HzKR127-3.1 with serine. Thereafter, the antibody was temporarily expressed in cells, and purified, and the affinity was then determined.

As a result, it was revealed that the affinity of the HzKR127-3.2 was $4.93 \times 10^{-10}$ M, the value of which was 1.6 folds higher than that of the HzKR127-3.1. Also, the analysis results showed that such a rise in affinity was mainly caused by a rise in binding rate (Table 1 and FIGS. 2 and 3D).

EXAMPLE 3

Analysis of Potential Immunogenicity of HzKR127-3.2

The VH and VL sequences of the HzKR127 and HzKR127-3.2 were analyzed to check whether there was a potential T cell epitope binding to MHC II molecules (HLA-DR). Because a peptide-MHC II complex was recognized by helper T cells and thus promoted differentiation of the helper T cells to stimulate an immune response, the presence of the potential T cell epitope was determined to reduce potential immunogenicity. The results are listed in the following Table 2.

As a result, as listed in Table 2, it was revealed that the potential T cell epitopes were positioned at a replication fork (HCDR2/FR3) between HCDR2 and FR3 of the HzKR127 and a replication fork (FR2/LCDR2) between FR2 and LCDR2 of the VL, but all the potential T cell epitopes were removed from the HzKR127-3.2 antibody according to the present invention in the case of the HCDR2/FR3 and the FR2 of VL, and most of the potential T cell epitopes were also removed in the case of the FR2/LCDR2, suggesting that the HzKR127-3.2 had remarkably reduced immunogenicity, compared to the HzKR127.

TABLE 2

| | Antibody | | | | | |
| --- | --- | --- | --- | --- | --- | --- |
| | HzKR127 | HzKR127-3.2 | HzKR127 | HzKR127-3.2 | HzKR127 | HzKR127-3.2 |
| | Location | | | | | |
| | HCDR2/FR3 | | FR2 in VL | | FR2/LCDR2 | |
| | Peptide sequence | | | | | |
| | YNGKFKGKA | YAQKFQGRV | WLLQKPGQS | WLLQKPGQP | IYLVSKLDS | IYLVSNRDS |
| MHC Class II molecules that Bind to peptide | DRB1_0801 | | DRB1_0305 | | DRB1_0301 | DRB1_0402 |
| | DRB1_0802 | | DRB1_0309 | | DRB1_0305 | DRB1_0404 |
| | DRB1_0804 | | DRB1_0401 | | DR31_0306 | DRB1_0405 |
| | DRB1_0806 | | DRB1_0426 | | DRB1_0307 | DRB1_0408 |
| | DRB1_0813 | | DRB1_0802 | | DRB1_0308 | DRB1_0410 |
| | DRB1_0817 | | DRB1_1101 | | DRB1_0309 | DRB1_0423 |
| | DRB1_1307 | | DRB1_1114 | | DRB1_0311 | DRB1_1102 |

TABLE 2-continued

| Antibody | | | | | |
|---|---|---|---|---|---|
| HzKR127 | HzKR127-3.2 | HzKR127 | HzKR127-3.2 | HzKR127 | HzKR127-3.2 |
| HCDR2/FR3 | | FR2 in VL | | FR2/LCDR2 | |
| Peptide sequence | | | | | |
| YNGKFKGKA | YAQKFQGRV | WLLQKPGQS | WLLQKPGQP | IYLVSKLDS | IYLVSNRDS |
| | | DRB1_1120 | | DRB1_0801 | DRB1_1121 |
| | | DRB1_1128 | | DRB1_0802 | DRB1_1322 |
| | | DRB1_1302 | | DR31_0804 | DRB5_0101 |
| | | DRB1_1305 | | DRB1_0806 | |
| | | DRB1_1307 | | DRB1_0813 | |
| | | DRB1_1323 | | DRB1_0817 | |
| | | DRB5_0101 | | DRB1_1101 | |
| | | DRB5_0105 | | DRB1_1102 | |
| | | | | DRB1_1104 | |
| | | | | DRB1_1106 | |
| | | | | DRB1_1107 | |
| | | | | DRB1_1114 | |
| | | | | DRB1_1120 | |
| | | | | DRB1_1121 | |
| | | | | DRE1_1128 | |
| | | | | DRB1_1301 | |
| | | | | DRB1_1302 | |
| | | | | DRB1_1304 | |
| | | | | DRB1_1305 | |
| | | | | DRB1_1307 | |
| | | | | DRB1_1311 | |
| | | | | DRB1_1321 | |
| | | | | DRB1_1322 | |
| | | | | DRB1_1323 | |
| | | | | DRB1_1327 | |
| | | | | DRB1_1328 | |
| Total number | 7 | 0 | 15 | 0 | 33 | 10 |

EXAMPLE 4

Analysis of Specificity of HzKR127-3.2

To check the antigen-binding specificity of HzKR127-3.2, a series of GST-pre-S1 ($1^{st}$ to $56^{th}$ amino acids) proteins having alanine-substituted mutations at respective positions the pre-S1 epitopes were expressed in E. coli, and then subjected, together with KR127 or HzKR127-3.2, to Western blot analysis.

As a result, as shown in FIG. 4A, it was revealed that the HzKR127-3.2 had the same epitope specificity as the KR127.

Also, to determine whether the HzKR127-3.2 had no off-target activity, flow cytometry was performed. To prepare pre-S1-expressing cells (293T-S1-L1) as a positive control, pre-S1 ($37^{th}$ to $47^{th}$ amino acids) was fused into the N terminus of a L1CAM (L1 cell adhesion molecule) protein. Thereafter, the fusion protein was temporarily expressed in the HEK293T cells.

As a result, as shown in FIG. 4B, it was revealed that the HzKR127-3.2 bound to surfaces of the 293T-S1-L1 cells as the pre-S1 positive cells, but did not bind to pre-S1-negative cells (HEK293T), L1CAM-overexpressing human cholangiocarcinoma cells (SCK-L1), human renal cancer cells (ACHN), murine melanoma cells (B16F1), and Chinese hamster ovary cells (CHO cells).

EXAMPLE 5

Determination of HBV Neutralizing Activity of HzKR127-3.2

Because the HzKR127-3.2 had a higher affinity to the pre-S1 antigen than the KR127, the virus neutralizing activities were compared through an in vitro HBV neutralization assay. HepaRG cells pre-treated with different concentrations (0.2 to 200 μg/mL) of each of the antibodies were infected with HBV particles that were the adr or ayw subtype. The infected cells were cultured for 10 days, and the culture media were replaced with fresh one once every other day. After 10 days of the infection, a level of HBsAg secreted from the infected cells was measured using ELISA. The results are shown in FIG. 5.

As a result, it was revealed that the HBsAg secretion rate decreased depending on an increase in concentration of the antibody, indicating that the HzKR127-3.2 antibody according to the present invention had neutralization specificity and suggesting that the HzKR127-3.2 antibody had an enhanced virus-neutralizing activity against both of the adr and ayw subtypes, compared to the KR127.

From the aforementioned description, persons having ordinary skill in the art will understand that the present invention may be implemented in other specific forms so that various modifications and changes are made to the exemplary embodiments thereof without departing from the scope and spirit of the present invention. Therefore, it should be understood that the exemplary embodiments disclosed above are illustrative in all aspects, but not intended to limit the present invention. Accordingly, it should be interpreted that all modifications and changes or modified and changed forms derived from the technical idea of the present invention fall within the scope of the present invention. Therefore, the scope of the present invention is defined not by the detailed description and embodiments, but by the following claims and their equivalents, and all differences within the scope will be construed as being included in the present invention.

What is claimed is:

1. An antibody binding specifically to a surface antigen pre-S1 of hepatitis B virus (HBV), wherein the antibody comprises a heavy-chain variable region comprising a heavy chain CDR1 set forth in SEQ ID NO: 2; a heavy chain CDR2 set forth in SEQ ID NO: 24; and a heavy chain CDR3 set forth in SEQ ID NO: 21, and a light-chain variable region comprising a light chain CDR1 set forth in SEQ ID NO: 9; a light chain CDR2 set forth in SEQ ID NO: 27; and a light chain CDR3 set forth in SEQ ID NO: 13.

2. The antibody of claim 1, wherein the antibody comprises a heavy-chain variable region set forth in SEQ ID NO: 30, and a light-chain variable region set forth in SEQ ID NO: 31.

3. An antibody binding specifically to a surface antigen pre-S1 of hepatitis B virus (HBV), wherein the antibody comprises a heavy-chain variable region set forth in SEQ ID NO: 23, and a light-chain variable region set forth in SEQ ID NO: 31.

4. The antibody of claim 1, wherein the antibody is a humanized antibody.

5. A polynucleotide coding for the antibody defined in claim 1.

6. An expression vector comprising the polynucleotide defined in claim 5.

7. A non-human transformant comprising the expression vector defined in claim 6.

8. A pharmaceutical composition for preventing or treating hepatitis B virus (HBV) infection, comprising the antibody defined in claim 1.

9. The pharmaceutical composition of claim 8, wherein the composition is for preventing or treating hepatitis B.

10. A method of providing information for diagnosis of hepatitis B virus (HBV) infection, comprising:
    detecting a pre-S1 protein, which is present in a biological sample isolated from a subject suspected to have HBV infection, through an antigen-antibody reaction using the antibody defined in claim 1.

11. The method of claim 10, wherein the method is for providing information for diagnosis of hepatitis B.

12. A composition for detecting hepatitis B virus (HBV), comprising the antibody defined in claim 1.

13. The composition of claim 12, wherein the composition is for diagnosis of hepatitis B.

14. A kit for detecting hepatitis B virus (HBV), comprising the composition defined in claim 12.

15. The antibody of claim 3, wherein the antibody is a humanized antibody.

16. A polynucleotide coding for the antibody defined in claim 3.

17. An expression vector comprising the polynucleotide defined in claim 16.

18. A non-human transformant comprising the expression vector defined in claim 17.

19. A pharmaceutical composition for preventing or treating hepatitis B virus (HBV) infection, comprising the antibody defined in claim 3.

20. The pharmaceutical composition of claim 19, wherein the composition is for preventing or treating hepatitis B.

21. A method of providing information for diagnosis of hepatitis B virus (HBV) infection, comprising:
    detecting a pre-S1 protein, which is present in a biological sample isolated from a subject suspected to have HBV infection, through an antigen-antibody reaction using the antibody defined in claim 3.

22. The method of claim 21, wherein the method is for providing information for diagnosis of hepatitis B.

23. A composition for detecting hepatitis B virus (HBV), comprising the antibody defined in claim 3.

24. The composition of claim 23, wherein the composition is for diagnosis of hepatitis B.

25. A kit for detecting hepatitis B virus (HBV), comprising the composition defined in claim 23.

* * * * *

```
                         SEQUENCE LISTING

<160> NUMBER OF SEQ ID NOS: 39

<210> SEQ ID NO 1
<211> LENGTH: 30
<212> TYPE: PRT
<213> ORGANISM: Artificial Sequence
<220> FEATURE:
<223> OTHER INFORMATION: FR1 in Heavy Chain of KR127

<400> SEQUENCE: 1

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser
            20                  25                  30

<210> SEQ ID NO 2
<211> LENGTH: 5
<212> TYPE: PRT
<213> ORGANISM: Artificial Sequence
<220> FEATURE:
<223> OTHER INFORMATION: CDR1 in Heavy Chain of KR127, HzKR127-3.1,
      HzKR127-3.2

<400> SEQUENCE: 2

Ser Ser Trp Met Asn
1               5

<210> SEQ ID NO 3
<211> LENGTH: 14
<212> TYPE: PRT
<213> ORGANISM: Artificial Sequence
<220> FEATURE:
<223> OTHER INFORMATION: FR2 in Heavy Chain of KR127

<400> SEQUENCE: 3

Trp Val Lys Gln Arg Pro Gly Gln Gly Leu Glu Trp Ile Gly
1               5                   10

<210> SEQ ID NO 4
<211> LENGTH: 17
<212> TYPE: PRT
<213> ORGANISM: Artificial Sequence
<220> FEATURE:
<223> OTHER INFORMATION: CDR2 in KR127

<400> SEQUENCE: 4

Arg Ile Tyr Pro Gly Asp Gly Asp Thr Asn Tyr Asn Gly Lys Phe Lys
1               5                   10                  15

Gly

<210> SEQ ID NO 5
<211> LENGTH: 32
<212> TYPE: PRT
<213> ORGANISM: Artificial Sequence
<220> FEATURE:
<223> OTHER INFORMATION: FR3 in Heavy Chain of KR127
```

-continued

```
<400> SEQUENCE: 5

Lys Ala Thr Leu Thr Ala Asp Lys Ser Ser Thr Ala Tyr Met Gln
1               5                   10                  15

Leu Ser Ser Leu Thr Ser Val Asp Ser Ala Val Tyr Phe Cys Ala Arg
                20                  25                  30

<210> SEQ ID NO 6
<211> LENGTH: 6
<212> TYPE: PRT
<213> ORGANISM: Artificial Sequence
<220> FEATURE:
<223> OTHER INFORMATION: CDR3 in Heavy Chain of KR127

<400> SEQUENCE: 6

Glu Tyr Asp Glu Ala Tyr
1               5

<210> SEQ ID NO 7
<211> LENGTH: 11
<212> TYPE: PRT
<213> ORGANISM: Artificial Sequence
<220> FEATURE:
<223> OTHER INFORMATION: FR4 in Heavy Chain of KR127

<400> SEQUENCE: 7

Trp Gly Gln Gly Thr Leu Val Thr Val Ser Ala
1               5                   10

<210> SEQ ID NO 8
<211> LENGTH: 23
<212> TYPE: PRT
<213> ORGANISM: Artificial Sequence
<220> FEATURE:
<223> OTHER INFORMATION: FR1 in Light chain of KR127

<400> SEQUENCE: 8

Asp Ile Leu Met Thr Gln Thr Pro Leu Ile Leu Ser Val Thr Ile Gly
1               5                   10                  15

Gln Pro Ala Ser Ile Ser Cys
                20

<210> SEQ ID NO 9
<211> LENGTH: 16
<212> TYPE: PRT
<213> ORGANISM: Artificial Sequence
<220> FEATURE:
<223> OTHER INFORMATION: CDR1 in Light chain of KR127, HzKR127-3.1 and
      HzKR127-3.2

<400> SEQUENCE: 9

Lys Ser Ser Gln Ser Leu Leu Tyr Ser Asn Gly Lys Thr Tyr Leu Asn
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: FR2 in Light chain of KR127

<400> SEQUENCE: 10

Trp Leu Leu Gln Arg Pro Gly Gln Ser Pro Lys Arg Leu Ile Tyr
1               5                   10                  15
```

<210> SEQ ID NO 11
<211> LENGTH: 7
<212> TYPE: PRT
<213> ORGANISM: Artificial Sequence
<220> FEATURE:
<223> OTHER INFORMATION: CDR2 in Light chain of KR127

<400> SEQUENCE: 11

Leu Val Ser Lys Leu Asp Ser
1               5

<210> SEQ ID NO 12
<211> LENGTH: 32
<212> TYPE: PRT
<213> ORGANISM: Artificial Sequence
<220> FEATURE:
<223> OTHER INFORMATION: FR3 in Light chain of KR127

<400> SEQUENCE: 12

Gly Val Pro Asp Arg Phe Thr Gly Ser Gly Ser Gly Thr Asp Phe Thr
1               5                   10                  15

Leu Lys Ile Ile Arg Val Glu Ala Glu Asp Leu Gly Val Tyr Tyr Cys
            20                  25                  30

<210> SEQ ID NO 13
<211> LENGTH: 9
<212> TYPE: PRT
<213> ORGANISM: Artificial Sequence
<220> FEATURE:
<223> OTHER INFORMATION: CDR3 in Light chain of KR127, HzKR127-3.1 and
      HzKR127-3.2

<400> SEQUENCE: 13

Val Gln Gly Thr His Phe Pro Gln Thr
1               5

<210> SEQ ID NO 14
<211> LENGTH: 11
<212> TYPE: PRT
<213> ORGANISM: Artificial Sequence
<220> FEATURE:
<223> OTHER INFORMATION: FR4 in Light chain of KR127

<400> SEQUENCE: 14

Phe Gly Gly Gly Thr Lys Leu Glu Ile Lys Arg
1               5                   10

<210> SEQ ID NO 15
<211> LENGTH: 115
<212> TYPE: PRT
<213> ORGANISM: Artificial Sequence
<220> FEATURE:
<223> OTHER INFORMATION: Heavy chain variable region of KR127

<400> SEQUENCE: 15

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Asn Tyr Asn Gly Lys Phe
    50                  55                  60

Lys Gly Lys Ala Thr Leu Thr Ala Asp Lys Ser Ser Ser Thr Ala Tyr
65                  70                  75                  80

```
Met Gln Leu Ser Ser Leu Thr Ser Val Asp Ser Ala Val Tyr Phe Cys
            85                  90                  95

Ala Arg Glu Tyr Asp Glu Ala Tyr Trp Gly Gln Gly Thr Leu Val Thr
            100                 105                 110

Val Ser Ala
        115

<210> SEQ ID NO 16
<211> LENGTH: 113
<212> TYPE: PRT
<213> ORGANISM: Artificial Sequence
<220> FEATURE:
<223> OTHER INFORMATION: Light chain variable region of KR127

<400> SEQUENCE: 16

Asp Ile Leu Met Thr Gln Thr Pro Leu Ile Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ile Arg Val Glu Ala Glu Asp Leu Gly Val Tyr Tyr Cys Val Gln Gly
                85                  90                  95

Thr His Phe Pro Gln Thr Phe Gly Gly Gly Thr Lys Leu Glu Ile Lys
            100                 105                 110

Arg

<210> SEQ ID NO 17
<211> LENGTH: 30
<212> TYPE: PRT
<213> ORGANISM: Artificial Sequence
<220> FEATURE:
<223> OTHER INFORMATION: FR1 in Heavy chain of HzKR127-3.1 and 3.2

<400> SEQUENCE: 17

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: FR2 in Heavy chain of HzKR127-3.1 and 3.2

<400> SEQUENCE: 18

Trp Val Arg Gln Ala Pro Gly Gln Gly Leu Glu Trp Met Gly
1               5                   10

<210> SEQ ID NO 19
<211> LENGTH: 17
<212> TYPE: PRT
<213> ORGANISM: Artificial Sequence
<220> FEATURE:
<223> OTHER INFORMATION: CDR2 in Heavy chain of HzKR127-3.1
```

```
<400> SEQUENCE: 19

Arg Ile Tyr Pro Gly Asp Gly Asp Thr Asn Tyr Ala Gln Lys Phe Gln
1               5                   10                  15

Gly

<210> SEQ ID NO 20
<211> LENGTH: 32
<212> TYPE: PRT
<213> ORGANISM: Artificial Sequence
<220> FEATURE:
<223> OTHER INFORMATION: FR3 in Heavy chain of HzKR127-3.1 and 3.2

<400> SEQUENCE: 20

Arg Val Thr Met Thr Ala Asp Lys Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 21
<211> LENGTH: 6
<212> TYPE: PRT
<213> ORGANISM: Artificial Sequence
<220> FEATURE:
<223> OTHER INFORMATION: CDR3 in Heavy chain of HzKR127-3.1 and 3.2

<400> SEQUENCE: 21

Glu Tyr Ala Glu Ala Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: FR4 in Heavy chain of HzKR127-3.1 and 3.2

<400> SEQUENCE: 22

Trp Gly Gln Gly Thr Leu Val Thr Val Ser Ser
1               5                   10

<210> SEQ ID NO 23
<211> LENGTH: 115
<212> TYPE: PRT
<213> ORGANISM: Artificial Sequence
<220> FEATURE:
<223> OTHER INFORMATION: Heavy chain variable region of HzKR127-3.1

<400> SEQUENCE: 23

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Asn Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Glu Tyr Ala Glu Ala Tyr Trp Gly Gln Gly Thr Leu Val Thr
            100                 105                 110

Val Ser Ser
        115

<210> SEQ ID NO 24
<211> LENGTH: 17
<212> TYPE: PRT
<213> ORGANISM: Artificial Sequence
<220> FEATURE:
<223> OTHER INFORMATION: CDR2 in Heavy chain of HzKR127-3.2

<400> SEQUENCE: 24

Arg Ile Tyr Pro Gly Asp Gly Asp Thr Ser Tyr Ala Gln Lys Phe Gln
1               5                   10                  15

Gly

<210> SEQ ID NO 25
<211> LENGTH: 23
<212> TYPE: PRT
<213> ORGANISM: Artificial Sequence
<220> FEATURE:
<223> OTHER INFORMATION: FR1 in Light chain of HzKR127-3.1 and 3.2

<400> SEQUENCE: 25

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 26
<211> LENGTH: 15
<212> TYPE: PRT
<213> ORGANISM: Artificial Sequence
<220> FEATURE:
<223> OTHER INFORMATION: FR2 in Light chain of HzKR127-3.1 and 3.2

<400> SEQUENCE: 26

Trp Leu Leu Gln Lys Pro Gly Gln Pro Pro Gln Arg Leu Ile Tyr
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: CDR2 in Light chain of HzKR127-3.1 and 3.2

<400> SEQUENCE: 27

Leu Val Ser Asn Arg Asp Ser
1               5

<210> SEQ ID NO 28
<211> LENGTH: 32
<212> TYPE: PRT
<213> ORGANISM: Artificial Sequence
<220> FEATURE:
<223> OTHER INFORMATION: FR3 in Light chain of HzKR127-3.1 and 3.2

<400> SEQUENCE: 28

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

```
<210> SEQ ID NO 29
<211> LENGTH: 11
<212> TYPE: PRT
<213> ORGANISM: Artificial Sequence
<220> FEATURE:
<223> OTHER INFORMATION: FR4 in Light chain of HzKR127-3.1 and 3.2

<400> SEQUENCE: 29

Phe Gly Gly Gly Thr Lys Val Glu Ile Lys Arg
1               5                   10

<210> SEQ ID NO 30
<211> LENGTH: 115
<212> TYPE: PRT
<213> ORGANISM: Artificial Sequence
<220> FEATURE:
<223> OTHER INFORMATION: Heavy chain variable region of HzKR127-3.2

<400> SEQUENCE: 30

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Met Asn Trp Val Arg Gln Ala Pro Gly Gln Gly Leu Glu Trp Met
        35                  40                  45

Gly Arg Ile Tyr Pro Gly Asp Gly Asp Thr Ser Tyr Ala Gln Lys Phe
    50                  55                  60

Gln Gly Arg Val Thr Met Thr Ala Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Ala Glu Ala Tyr Trp Gly Gln Gly Thr Leu Val Thr
            100                 105                 110

Val Ser Ser
        115

<210> SEQ ID NO 31
<211> LENGTH: 113
<212> TYPE: PRT
<213> ORGANISM: Artificial Sequence
<220> FEATURE:
<223> OTHER INFORMATION: Light chain variable region of HzKR127-3.1 and
        3.2

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Pro
        35                  40                  45

Pro Gln Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

Arg
```

```
<210> SEQ ID NO 32
<211> LENGTH: 110
<212> TYPE: PRT
<213> ORGANISM: Human

<400> SEQUENCE: 32

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Thr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Trp Gly Gln Gly Thr Leu Val Thr Val Ser Ser
            100                 105                 110

<210> SEQ ID NO 33
<211> LENGTH: 115
<212> TYPE: PRT
<213> ORGANISM: artificial sequence
<220> FEATURE:
<223> OTHER INFORMATION: HzKR127 heavy chain

<400> SEQUENCE: 33

Gln Val Gln Leu Gln Gln Ser Gly Ala Glu Val Val Lys Pro Gly Ala
1               5                   10                  15

Ser Val Lys Val Ser Cys Lys Ala Ser Gly Tyr Ala Phe Ser Ser Ser
                20                  25                  30

Trp Met Asn Trp Val Arg Gln Ala Pro Gly Gln Gly Leu Glu Trp Ile
            35                  40                  45

Gly Arg Ile Tyr Pro Gly Asp Gly Asp Thr Asn Thr Ala Gln Lys Phe
        50                  55                  60

Gln Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Thr Phe Cys
                85                  90                  95

Ala Arg Glu Tyr Asp Glu Ala Tyr Trp Gly Gln Gly Thr Leu Val Thr
            100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: HzKR127-3 heavy chain

<400> SEQUENCE: 34

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
                20                  25                  30
```

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Thr Ala Gln Lys Phe
 50                  55                  60

Gln Gly Arg Val Thr Met Thr Ala Asp Lys Ser Thr Ser Thr Val Tyr
 65                  70                  75                  80

Met Glu Leu Ser Ser Leu Arg Ser Glu Asp Thr Ala Val Thr Tyr Cys
                85                  90                  95

Ala Arg Glu Tyr Asp Glu Ala Tyr Trp Gly Gln Gly Thr Leu Val Thr
                100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: HzKR127-3.1 heavy chain

<400> SEQUENCE: 35

Gln Val Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Asn Thr Ala Gln Lys Phe
 50                  55                  60

Gln Gly Arg Val Thr Met Thr Ala Asp Lys Ser Thr Ser Thr Val Tyr
 65                  70                  75                  80

Met Glu Leu Ser Ser Leu Arg Ser Glu Asp Thr Ala Val Thr Tyr Cys
                85                  90                  95

Ala Arg Glu Tyr Ala Glu Ala Tyr Trp Gly Gln Gly Thr Leu Val Thr
                100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: HzKR127-3.2 heavy chain

<400> SEQUENCE: 36

Gln Val Gln Leu Gln Gln Ser Gly Ala Glu Val Lys Lys Pro Gly Ala
 1               5                  10                  15

Ser Val Lys Val Ser Cys Lys Ala Ser Gly Tyr Thr Phe Thr Ser Ser
                20                  25                  30

Trp Met Asn Trp Val Arg Gln Ala Pro Gly Gln Gly Leu Glu Trp Met
            35                  40                  45

Gly Arg Ile Tyr Pro Gly Asp Gly Asp Thr Ser Thr Ala Gln Lys Phe
 50                  55                  60

Gln Gly Arg Val Thr Met Thr Ala Asp Lys Ser Thr Ser Thr Val Tyr
 65                  70                  75                  80

Met Glu Leu Ser Ser Leu Arg Ser Glu Asp Thr Ala Val Thr Tyr Cys
                85                  90                  95

Ala Arg Glu Tyr Ala Glu Ala Tyr Trp Gly Gln Gly Thr Leu Val Thr
            100                 105                 110

Val Ser Ser
        115

<210> SEQ ID NO 37
<211> LENGTH: 113
<212> TYPE: PRT
<213> ORGANISM: Human

<400> SEQUENCE: 37

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Leu Thr Phe Gly Gly Gly Thr Lys Val Glu Ile Lys
            100                 105                 110

Arg

<210> SEQ ID NO 38
<211> LENGTH: 113
<212> TYPE: PRT
<213> ORGANISM: Artificial Sequence
<220> FEATURE:
<223> OTHER INFORMATION: HzKR127 light chain

<400> SEQUENCE: 38

Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Tyr Trp Leu Leu Gln Lys Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
            100                 105                 110

Arg

<210> SEQ ID NO 39
<211> LENGTH: 113
<212> TYPE: PRT
<213> ORGANISM: Artificial Sequence
<220> FEATURE:
<223> OTHER INFORMATION: HzKR127-3 light chain

```
<400> SEQUENCE: 39

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Tyr Trp Leu Leu Gln Lys Pro Gly Gln Pro
        35                  40                  45

Pro Gln Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Gln Thr Phe Gly Gly Gly Thr Lys Val Glu Ile Lys
                100                 105                 110

Arg
```